United States Patent
Cinar et al.

(10) Patent No.: US 11,940,437 B2
(45) Date of Patent: Mar. 26, 2024

(54) DETERMINING ULTIMATE WATERFLOOD RESIDUAL OIL SATURATION

(71) Applicant: SAUDI ARABIAN OIL COMPANY, Dhahran (SA)

(72) Inventors: Yildiray Cinar, Dhahran Hills (SA); Tony R. Pham, Dhahran (SA); Naseem J. Al-Dawood, Safwa (SA)

(73) Assignee: Saudi Arabian Oil Company, Dhahran (SA)

( * ) Notice: Subject to any disclaimer, the term of this patent is extended or adjusted under 35 U.S.C. 154(b) by 864 days.

(21) Appl. No.: 16/638,014

(22) PCT Filed: Aug. 7, 2018

(86) PCT No.: PCT/US2018/045632
§ 371 (c)(1),
(2) Date: Feb. 10, 2020

(87) PCT Pub. No.: WO2019/032597
PCT Pub. Date: Feb. 14, 2019

(65) Prior Publication Data
US 2020/0173975 A1  Jun. 4, 2020

Related U.S. Application Data

(60) Provisional application No. 62/542,508, filed on Aug. 8, 2017.

(51) Int. Cl.
*E21B 49/00* (2006.01)
*G01N 13/00* (2006.01)
*G01N 33/24* (2006.01)

(52) U.S. Cl.
CPC ........... *G01N 33/241* (2013.01); *G01N 13/00* (2013.01); *E21B 49/00* (2013.01)

(58) Field of Classification Search
CPC .................. E21B 49/00; E21B 43/16
(Continued)

(56) References Cited

U.S. PATENT DOCUMENTS

| 6,178,807 B1 | 1/2001 | Baldwin et al. |
| 6,185,985 B1 | 2/2001 | Fleury et al. |

(Continued)

FOREIGN PATENT DOCUMENTS

| WO | WO2012123863 | 9/2012 |

OTHER PUBLICATIONS

GCC Examination Report in GCC Appln. GC 2018-35790, dated Jan. 13, 2020, 4 pages.
(Continued)

*Primary Examiner* — Zakiya W Bates
*Assistant Examiner* — Ashish K Varma
(74) *Attorney, Agent, or Firm* — Fish & Richardson P.C.

(57) ABSTRACT

A method of determining waterflood residual oil saturation includes testing, in a laboratory multispeed centrifuge test, a reservoir core sample to obtain a set of average water saturation ($S_{w,avg}$) and imbibition capillary pressure ($P_{ci}$) data points, applying a best-fit smoothing function to the data points to obtain a best-fit average saturation curve, converting the best-fit average saturation curve to an outlet-face saturation curve, applying a best-fit straight line to the outlet-face saturation curve associated with a substantially constant outlet water saturation and changing imbibition capillary pressure, and determining a waterflood residual oil saturation ($S_{orw}$) of the core sample. The waterflood residual oil saturation is associated with a point on the outlet-face saturation curve where the best-fit straight line deviates from the outlet-face saturation curve.

22 Claims, 4 Drawing Sheets

(58) Field of Classification Search
USPC .................................................... 166/252.2
See application file for complete search history.

(56) References Cited

U.S. PATENT DOCUMENTS

| | | | |
|---|---|---|---|
| 6,415,649 | B1 | 7/2002 | Spinler et al. |
| 10,815,416 | B2* | 10/2020 | Jin .......................... C09K 8/665 |
| 2006/0047432 | A1 | 3/2006 | Egermann et al. |
| 2006/0116828 | A1 | 6/2006 | Chen et al. |
| 2016/0196369 | A1* | 7/2016 | Ramsay .................. E21B 49/00 703/10 |
| 2018/0163533 | A1* | 6/2018 | Wlodarczyk ............ G01V 1/40 |
| 2020/0173975 | A1* | 6/2020 | Cinar ...................... G01N 13/00 |
| 2021/0355824 | A1* | 11/2021 | Pal ...................... E21B 49/0875 |

OTHER PUBLICATIONS

International Search Report and Written Opinion of the International Searching Authority issued in International Application No. PCT/US2018/045632 dated Nov. 29, 2018; 10 pages.

Bruchbacher, Julia; "Imbibition Capillary Pressure Curve Modelling for Two-Phase Flow in Mixed-West Reservoirs"; University of Stavanger; Jun. 17, 2013; 92 pages.

GCC Examination Report in GCC Appln. GC 2018-35790, dated May 14, 2020, 4 pages.

Agnia et al., "Oil-water relative permeability data for reservoir simulation input, part I—systematic quality assessment and consistency evaluation," International Petroleum Technology Conference Paper IPTC-18132, Dec. 10-12, 2014, 33 pages.

Al-Housani et al., "Using residual oil saturation (Sor) to reduce uncertainty in reservoir modelling—A case study," SPE-161531, Presented at the Abu Dhabi International Petroleum Exhibition & Conference, Abu Dhabi, UAE, Nov. 11-14, 2012; Society of Petroleum Engineers, 2012, 15 pages.

Al-Sabea et al., "Residual oil saturation analysis of the Burgan formation in the greater Burgan Field Kuwait," SPE-88682, Presented at the Abu Dhabi International Petroleum Exhibition & Conference, Abu Dhabi, UAE, Oct. 10-13, 2004; Society of Petroleum Engineers, 2004, 18 pages.

Alyafei & Blunt, "The effect of wettability on capillary trapping in carbonates," Advances in Water Resources 90, 36-50, 2016, 15 pages.

Batias et al., "Field and laboratory observations of remaining oil saturations in a light oil reservoir flooded by a low salinity aquifer," Soc. Core Analysts Symposium Paper, Sep. 2009, Jan. 2009, 12 pages.

Behairy et al., "Evaluation of residual oil saturation after waterflood in a large carbonate field in Oman," Presented at the SPWLA Middle East Regional Symposium, Abu Dhabi, UAE, Apr. 15-19, 2007; Society of Petrophysicists, 2007, 13 pages.

Behrenbruch, "Waterflood residual oil saturation—The Buffalo Field Timor Sea," Soc. Pet. Eng. Paper SPE-64282, 2000, 15 pages.

Blackwell, "An overview of in-situ methods for determining remaining oil saturations," Soc. Petroleum Eng. Paper SPE-13702, 1985, 16 pages.

Bruchbacher et al., "Modelling of the full envelope of capillary pressure curves from the centrifuge," SCA2014-003, presented at the Int. Symp. of the Soc. Of Core Analysts, Avignon, France Sep. 8-11, 2014, 13 pages.

Chen et al., "New Capillary Pressure Models for Parameter Estimation to Interpret Centrifuge Data," SPE 24045, Presented at the Western Regional Meeting, Bakersfield, California, Mar. 30-Apr. 1, 1992; Society of Petroleum Engineers, 1992, 8 pages.

Christiansen et al., "Estimating oil reserves in oil-water transition zones," SPE-59403, Presented at SPE Asia Pacific Conference on Integrated Modelling for Asset Management, Yokohama, Japan, Apr. 25-26, 2000; Society of Petroleum Engineers, 2000, 10 pages.

Christiansen et al., "Geometric Concerns for Accurate Measurement of Capillary Pressure Relationships with Centrifuge Methods," SPE Formation Evaluation, vol. 7, Issue 4, Dec. 1992, 6 pages.

Clerke et al., "Spontaneous imbibition of water into oil saturated M_1 bimodal limestone," IPTC Paper 17162, Presented at the Int. Petroleum Technology Conf, Beijing, China, Mar. 26-28, 2013; International Petroleum Conference, 2013, 19 pages.

Ferno et al., "Capillary Pressures by Fluid Saturation Profile Measurements During Centrifuge Rotation," Transp Porous Med, Nov. 2009, 80: 253-267.

Forbes, "Quantitative evaluation and correction of gravity effects on centrifuge capillary pressure curves," SCA-9734, Proc. of the Int. Symp. of the Soc. Core Analysts, Calgary, Sep. 7-10, 1997, 16 pages.

Hassler and Brunner, "Measurement of capillary pressures in small core samples," Trans. AIME 160, 14-123, 1945, 10 pages.

Kalam et al., "Importance of porous plate measurements on carbonates at pseudo reservoir conditions," SCA-2006-28, Proc. of the Int. Symp. of the Soc. Core Analysts, Trondheim, Sep. 12-16, 2006, 13 pages.

Kamath et al., "Understanding waterflood residual oil saturation of four carbonate rock types," SPE- 71505, Presented at the SPE Annual Technical Conference and Exhibition, New Orleans, Louisiana, Sep. 30-Oct. 3, 2001; Society of Petroleum Engineers, 2001, 10 pages.

Kamath et al., "Water/oil relative permeability endpoints of intermediate-wet low permeability rocks," SPE Formation Eval., Mar. 4-10, 1995, 7 pages.

Kennaird, "Residual oil saturations determined by core analysis," SPE-17686, Presented at the 7th Offshore South East Asia Conference, Singapore, Feb. 2-5, 1988; Soc. Petroleum Eng, 1988, 11 pages.

Khaledialidusti et al., "An innovative technique for determining residual and current oil saturations using a combination of log-inject-log and SWCT test methods, " Journal of Petroleum Science and Engineering, Oct. 2015, 135:618-625.

Lake, "Enhanced oil recovery," Prentice-Hall, Inc. New Jersey, 1989, p. 59, 550 pages.

Masalmeh & Jing, "Improved characterization and modeling of capillary transition zones in carbonate reservoirs," SPE 109094, Presented at the Int. Pet. Tech. Conf., Doha, Qatar, Nov. 21-23, 2005; SPE Reservoir Evaluation & Engineering, Apr. 2007, 14 pages.

Masalmeh and Jing, "Carbonate SCAL: Characterization of carbonate rock types for determination of saturation functions and residual oil saturations," Soc. Core Analysts Paper #2004-08, 2004, 12 pages.

Masalmeh and Jing, "The importance of sCAL in modelling remaining oil saturation in carbonate fields," Soc. Core analysts Symp. Paper 2008-03, 2008, 12 pages.

Masalmeh, "Determination of waterflooding residual oil saturation for mixed to oil-wet carbonate reservoir and its impact on EOR," Soc. Pet. Eng. Paper SPE-165981, 2013, 14 pages.

Masalmeh, "Impact of capillary forces on residual oil saturation and flooding experiment for mixed to oil-wet carbonate reservoirs," Soc. Core Analysts Symp. Paper 2012-11, 2012, 14 pages.

Mitchell et al., "The impact of reservoir confining stress on NMR T2 and pore frequency distribution in some carbonate samples," SCAL2007-20, Presented at the Int. Symp. of the Soc. Core Analysts, Calgary, Canada, Sep. 10-12, 2007.

Nordtvedt et al., "Estimation of Capillary Pressure and Relative Permeability Functions from Centrifuge experiments," SPE Reservoir engineering, Nov. 1993, 8(4): 292-298.

O'Meara et al., "Centrifuge measurements of capillary pressure: Part 1—outflow boundary condition," SPE-18296, SPE Reservoir Engineering, Feb. 1992; Society of Petroleum Engineers, 1992, 10 pages.

Okasha et al, "Evaluation of recovery efficiency and residual oil saturation of two distinct Arabian carbonate reservoirs," Soc. Core Analysts Paper 2003-37, 2005, 12 pages.

Pham and Al-Shahri, "Assessment of residual oil saturation in a large carbonate reservoir," Soc. Pet. Eng. Paper SPE-68069, 2001, 7 pages.

(56) References Cited

OTHER PUBLICATIONS

Ruth et al., "Calculation Of Capillary-pressure Curves From Data Obtained By The Centrifuge Method," The Log Analyst, Sep. 1991, 32(5), 11 pages.

Ryazanov et al., "Structure of residual oil as a function of wettability using pore-network modelling," Advances in Water Resour., 2014, 63: 11-21.

Slobod et al., "Use of centrifuge for determining connate water, residual oil and capillary pressure curves of small core samples," Petroleum Transactions, AIME, 1951, 192: 127-134.

Sorbie et al., "The structure of residual oil as a function of wettability alteration using pore-scale network modelling," Soc. Core Analysts Symposium Paper 2011-37, 2011, 12 pages.

Spearing et al., "Transition zone behavior: The measurement of bounding and scanning relative permeability and capillary pressure curves at reservoir conditions for a giant carbonate reservoir," Soc. Core Analysts Symposium Paper 2014-004, Nov. 2014, 14 pages.

Teklu et al., "A critical literature review of laboratory and field scale determination of residual oil saturation," SPE-164483, Presented at the SPE Production and Operations Symposium, Oklahoma City, Oklahoma, USA, Mar. 23-26, 2013; Society of Petroleum Engineers, 2013, 17 pages.

Teklu et al., "Residual oil saturation determination—case studies in sandstone and carbonate reservoirs," SPE-164825, Presented at the EAGE Annual Conference & Exhibition incorporating SPE Europe, London, United Kingdom, Jun. 10-13, 2013; Soc. Pet. Eng. 2013, 9 pages.

Tobola, "The contribution of oil production mechanisms as determined by a novel centrifuge technique," SCA-9617, Proc. of the Int. Symp. of the Soc. Core Analysts, Montpellier, France, Sep. 8-10, 1996, 8 pages.

Torsaeter, "An experimental study of water imbibition in chalk from the Ekofisk Field," Soc. Petroleum Eng. Paper SPE-12688, Apr. 1984, 12 pages.

Valenti et al., "A unified theory on residual oil saturation and irreducible water saturation," SPE Paper 77545, Presented at the SPE Annual Tech Conf & Exhib., San Antonio, TX, Sep. 29-Oct. 2, 2002; Society of Petroleum Engineers, 2002, 16 pages.

Verma et al., "Evaluation of residual oil saturation after waterflood in a carbonate reservoir," Soc. Pet. Eng. Reservoir Eng, 247-253, Nov. 1994, 7 pages.

Wahlheim et al., "Remaining oil saturation determination in Dukhan Arab C and Arab D reservoirs," Paper IPTC-17437, Presented at the International Petroleum Technology Conference, Doha, Qatar, Jan. 20-22, 2014; International Petroleum Technology Conference, 2014, 25 pages.

Wood et al., "Determining effective residual oil saturation for mixed wettability reservoirs: Endicott Field, Alaska," Soc. Pet. Eng. Paper SPE-22903, Oct. 6-9, 1991; Society of Petroleum Engineers, 1991, 8 pages.

* cited by examiner

DETERMINING ULTIMATE WATERFLOOD RESIDUAL OIL SATURATION

CLAIM OF PRIORITY

This application is a U.S. National Stage of PCT/US2018/045632 filed on Aug. 7, 2018, which claims priority to U.S. Provisional Patent Application No. 62/542,508, filed Aug. 8, 2017, the contents of which are hereby incorporated by reference.

TECHNICAL FIELD

This disclosure relates to determining properties of a reservoir core sample, that is, a core sample obtained from a hydrocarbon-carrying reservoir.

BACKGROUND

In the oil and gas industry, reservoir simulation is used to assess expected hydrocarbon recovery from the reservoir. Simulating a reservoir often includes retrieving a reservoir material sample and testing the reservoir material sample in a laboratory to estimate characteristics of the sample. The estimated characteristics can be extrapolated for a complete reservoir to estimate ultimate hydrocarbon recovery from the reservoir.

SUMMARY

This disclosure describes methods and systems for determining waterflood residual oil saturation of a reservoir sample, for example, to be used to simulate hydrocarbon recovery from a reservoir.

Some aspects of the disclosure encompass a method of determining waterflood residual oil saturation. The method includes testing, in a laboratory multispeed centrifuge test, a reservoir core sample to obtain a set of average water saturation ($S_{w,avg}$) and imbibition capillary pressure ($P_{ci}$) data points, and applying, with a controller, a best-fit smoothing function to the data points to obtain a best-fit average saturation curve, where the best-fit average saturation curve represents imbibition capillary pressure ($P_{ci}$) over average water saturation ($S_{w,avg}$). The method includes converting, with the controller, the best-fit average saturation curve to an outlet-face saturation curve, where the outlet-face saturation curve represents imbibition capillary pressure ($P_{ci}$) over outlet water saturation ($S_{w,outlet}$), and applying, with the controller, a best-fit straight line to the outlet-face saturation curve associated with a substantially constant outlet water saturation and changing imbibition capillary pressure. The method further includes determining, with the controller, a waterflood residual oil saturation ($S_{orw}$) of the core sample, where the waterflood residual oil saturation is associated with a point on the outlet-face saturation curve where the best-fit straight line deviates from the outlet-face saturation curve. The waterflood residual oil saturation ($S_{orw}$) represents the ratio of the volume of the oil trapped in pores of the reservoir core sample under waterflooding to the total volume of the pores of the reservoir core sample. The method further includes providing the waterflood residual oil saturation ($S_{orw}$).

This, and other aspects, can include one or more of the following features. Testing the reservoir core sample to obtain a set of average water saturation ($S_{w,avg}$) and imbibition capillary pressure ($P_{ci}$) data points can include determining average water saturation ($S_{w,avg}$) data points from measured volumes of expelled oil from the reservoir core sample for a set of rotational speeds of the centrifuge test, and determining imbibition capillary pressure ($P_{ci}$) using the following equation:

$$P_{ci} = \frac{1}{2}\Delta\rho\omega^2(r_3^2 - r_1^2),$$

where $\Delta\rho$ is a density difference between oil and water, $\omega$ is a rotational speed of the centrifuge of the centrifuge test, $r_3$ is a distance between an inlet end of the reservoir core sample and a rotational axis of the centrifuge, and $r_1$ is the distance between an outlet end of the reservoir core sample and the rotational axis of the centrifuge. Testing the reservoir core sample to obtain a set of water saturation ($S_{w,avg}$) and imbibition capillary pressure ($P_{ci}$) data points can include saturating the reservoir core sample with connate formation water and dead crude oil, placing the reservoir core sample in an imbibition bucket of the centrifuge, where the imbibition bucket is at least partially filled with injection water, setting a temperature in the imbibition bucket to a threshold reservoir temperature, rotating the reservoir core sample at a first rotational speed until no oil production from the reservoir core sample is observed, and rotating the reservoir core sample at a second rotational speed higher than the first rotational speed until no oil production from the reservoir core sample is observed. Applying a best-fit smoothing function to the data points to obtain a best-fit average saturation curve can include plotting the following equation for average water saturation ($S_{w,avg}$):

$$S_{w,avg} = 1 - a + \frac{1}{P_{ci}}\{b[1 - \exp(cP_{ci})] + d[1 - \exp(eP_{ci})]\},$$

where a, b, c, d, and e are best-fit matching parameters, and where parameters a and b affect a high-$P_{ci}$ section of the best-fit average saturation curve, parameters d and e affect a low-$P_{ci}$ section of the best-fit average saturation curve, and parameter c affects a transition section of the best-fit average saturation curve between the high-$P_{ci}$ section and the low-$P_{ci}$ section. Applying a best-fit smoothing function to the data points to obtain the best-fit average saturation curve can include applying a non-linear regression to the data points to obtain the best-fit average saturation curve. Converting the best-fit average saturation curve to the outlet-face saturation curve can include plotting the following equation for outlet water saturation $$(S_{w,outlet}): S_{w,outlet} = S_{w,avg} + P_{ci} \times \frac{dS_{w,avg}}{dP_{ci}},$$

where $dS_{w,avg}/dP_{ci}$ is the derivative of the equation for average water saturation ($S_{w,avg}$), and plotting the equation for outlet water saturation ($S_{w,outlet}$) provides a true laboratory negative imbibition capillary pressure ($P_{ci}$) curve. Determining the waterflood residual oil saturation ($S_{orw}$) of the core sample, where the waterflood residual oil saturation is associated with a point on the outlet-face saturation curve where the best-fit straight line deviates from the outlet-face saturation curve, can include identifying the point on the outlet-face saturation curve corresponding to $dS_{w,avg}/dP_{ci}$ being equal to approximately 0.01. The laboratory multispeed centrifuge test on the reservoir core sample can include an imbibition test of water displacing oil. Providing the waterflood residual oil saturation ($S_{orw}$) can include displaying the waterflood residual oil saturation ($S_{orw}$) in a display of a display device connected to the controller.

Certain aspects of the disclosure encompass a computer-implemented method of analyzing a reservoir core sample tested under a laboratory multispeed centrifuge test of water displacing oil. The computer-implemented method includes obtaining a set of average water saturation ($S_{w,avg}$) and imbibition capillary pressure ($P_{ci}$) data points from a laboratory multispeed centrifuge test of a reservoir core sample, applying, with a controller, a best-fit smoothing function to the data points to obtain a best-fit average saturation curve, where the best-fit average saturation curve represents imbibition capillary pressure ($P_{ci}$) over average water saturation ($S_{w,avg}$), converting, with the controller, the best-fit average saturation curve to an outlet-face saturation curve, where the outlet-face saturation curve represents imbibition capillary pressure ($P_{ci}$) over outlet water saturation ($S_{w,outlet}$), and applying, with the controller, a best-fit straight line to the outlet-face saturation curve associated with a substantially constant outlet water saturation and changing imbibition capillary pressure. The computer-implemented method further includes determining, with the controller, a waterflood residual oil saturation ($S_{orw}$) of the core sample, where the waterflood residual oil saturation is associated with a point on the outlet-face saturation curve where the best-fit straight line deviates from the outlet-face saturation curve. The waterflood residual oil saturation (Sores) represents the ratio of the volume of the oil trapped in pores of the reservoir core sample under waterflooding to the total volume of the pores of the reservoir core sample. The computer-implemented method further includes providing the waterflood residual oil saturation ($S_{orw}$).

This, and other aspects, can include one or more of the following features. Testing the reservoir core sample to obtain a set of average water saturation ($S_{w,avg}$) and imbibition capillary pressure ($P_{ci}$) data points can include determining average water saturation ($S_{w,avg}$) data points from measured volumes of expelled oil from the reservoir core sample for a set of rotational speeds of the centrifuge test, and determining imbibition capillary pressure ($P_{ci}$) using the following equation:

$$P_{ci} = \frac{1}{2}\Delta\rho\omega^2(r_3^2 - r_1^2),$$

where $\Delta\rho$ is a density difference between oil and water, $\omega$ is a rotational speed of the centrifuge of the centrifuge test, $r_3$ is a distance between an inlet end of the reservoir core sample and a rotational axis of the centrifuge, and $r_1$ is the distance between an outlet end of the reservoir core sample and the rotational axis of the centrifuge. Applying a best-fit smoothing function to the data points to obtain a best-fit average saturation curve can include plotting the following equation for average water saturation ($S_{w,avg}$):

$$S_{w,avg} = 1 - a + \frac{1}{P_{ci}}\{b[1 - \exp(cP_{ci})] + d[1 - \exp(eP_{ci})]\},$$

where a, b, c, d, and e are best-fit matching parameters, and where parameters a and b affect a high-$P_{ci}$ section of the best-fit average saturation curve, parameters d and e affect a low-$P_{ci}$ section of the best-fit average saturation curve, and parameter c affects a transition section of the best-fit average saturation curve between the high-$P_{ci}$ section and the low-$P_{ci}$ section. Applying a best-fit smoothing function to the data points to obtain the best-fit average saturation curve can include applying a non-linear regression to the data points to obtain the best-fit average saturation curve. Converting the best-fit average saturation curve to the outlet-face saturation curve can include plotting the following equation for outlet water saturation ($S_{w,outlet}$):

$$S_{w,outlet} = S_{w,avg} + P_{ci} \times \frac{dS_{w,avg}}{dP_{ci}},$$

where $dS_{w,avg}/dP_{ci}$ is the derivative of the equation for average water saturation ($S_{w,avg}$), and where plotting the equation for outlet water saturation ($S_{w,outlet}$) provides a true laboratory negative imbibition capillary pressure ($P_{ci}$) curve. Determining the waterflood residual oil saturation ($S_{orw}$) of the core sample, where the waterflood residual oil saturation is associated with a point on the outlet-face saturation curve where the best-fit straight line deviates from the outlet-face saturation curve, can include identifying the point on the outlet-face saturation curve corresponding to $dS_{w,avg}/dP_{ci}$ being equal to approximately 0.01. Providing the waterflood residual oil saturation ($S_{orw}$) can include displaying the waterflood residual oil saturation ($S_{orw}$) in a display of a display device connected to the controller.

Certain aspects of the disclosure encompass a computer-readable medium storing instructions operable when executed by one or more processors to perform operations. The operations include obtaining a set of average water saturation ($S_{w,avg}$) and imbibition capillary pressure ($P_{ci}$) data points from a laboratory multispeed centrifuge test of a reservoir core sample, applying a best-fit smoothing function to the data points to obtain a best-fit average saturation curve, where the best-fit average saturation curve represents imbibition capillary pressure ($P_{ci}$) over average water saturation ($S_{w,avg}$), converting the best-fit average saturation curve to an outlet-face saturation curve, where the outlet-face saturation curve represents imbibition capillary pressure ($P_{ci}$) over outlet water saturation ($S_{w,outlet}$), and applying a best-fit straight line to the outlet-face saturation curve associated with a substantially constant outlet water saturation and changing imbibition capillary pressure. The operations further include determining a waterflood residual oil saturation ($S_{orw}$) of the core sample, where the waterflood residual oil saturation is associated with a point on the outlet-face saturation curve where the best-fit straight line deviates from the outlet-face saturation curve. The waterflood residual oil saturation ($S_{orw}$) represents the ratio of the volume of the oil trapped in pores of the reservoir core sample under waterflooding to the total volume of the pores of the reservoir core sample. The operations further include providing the waterflood residual oil saturation ($S_{orw}$).

This, and other aspects, can include one or more of the following features. Testing the reservoir core sample to obtain a set of average water saturation ($S_{w,avg}$) and imbibition capillary pressure ($P_{ci}$) data points can include determining average water saturation ($S_{w,avg}$) data points from measured volumes of expelled oil from the reservoir core sample for a set of rotational speeds of the centrifuge test, and determining imbibition capillary pressure ($P_{ci}$) using the following equation:

$$P_{ci} = \frac{1}{2}\Delta\rho\omega^2(r_3^2 - r_1^2),$$

where $\Delta\rho$ is a density difference between oil and water, $\omega$ is a rotational speed of the centrifuge of the centrifuge test, $r_3$ is a distance between an inlet end of the reservoir core sample and a rotational axis of the centrifuge, and $r_1$ is the distance between an outlet end of the reservoir core sample and the rotational axis of the centrifuge.

Applying a best-fit smoothing function to the data points to obtain a best-fit average saturation curve can include plotting the following equation for average water saturation ($S_{w,avg}$):

$$S_{w,avg} = 1 - a + \frac{1}{P_{ci}}\{b[1 - \exp(cP_{ci})] + d[1 - \exp(eP_{ci})]\},$$

where a, b, c, d, and e are best-fit matching parameters, and where parameters a and b affect a high-$P_{ci}$ section of the best-fit average saturation curve, parameters d and e affect a low-$P_{ci}$ section of the best-fit average saturation curve, and parameter c affects a transition section of the best-fit average saturation curve between the high-$P_{ci}$ section and the low-$P_{ci}$ section. Applying a best-fit smoothing function to the data points to obtain the best-fit average saturation curve can include applying a non-linear regression to the data points to obtain the best-fit average saturation curve. Converting the best-fit average saturation curve to the outlet-face saturation curve can include plotting the following equation for outlet water saturation ($S_{w,outlet}$):

$$S_{w,outlet} = S_{w,avg} + P_{ci} \times \frac{dS_{w,avg}}{dP_{ci}},$$

where $dS_{w,avg}/dP_{ci}$ is the derivative of the equation for average water saturation ($S_{w,avg}$), and where plotting the equation for outlet water saturation ($S_{w,outlet}$) provides a true laboratory negative imbibition capillary pressure ($P_{ci}$) curve. Determining the waterflood residual oil saturation ($S_{orw}$) of the core sample, where the waterflood residual oil saturation is associated with a point on the outlet-face saturation curve where the best-fit straight line deviates from the outlet-face saturation curve, can include identifying the point on the outlet-face saturation curve corresponding to $dS_{w,avg}/dP_{ci}$ being equal to approximately 0.01.

The details of one or more implementations of the subject matter described in this disclosure are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
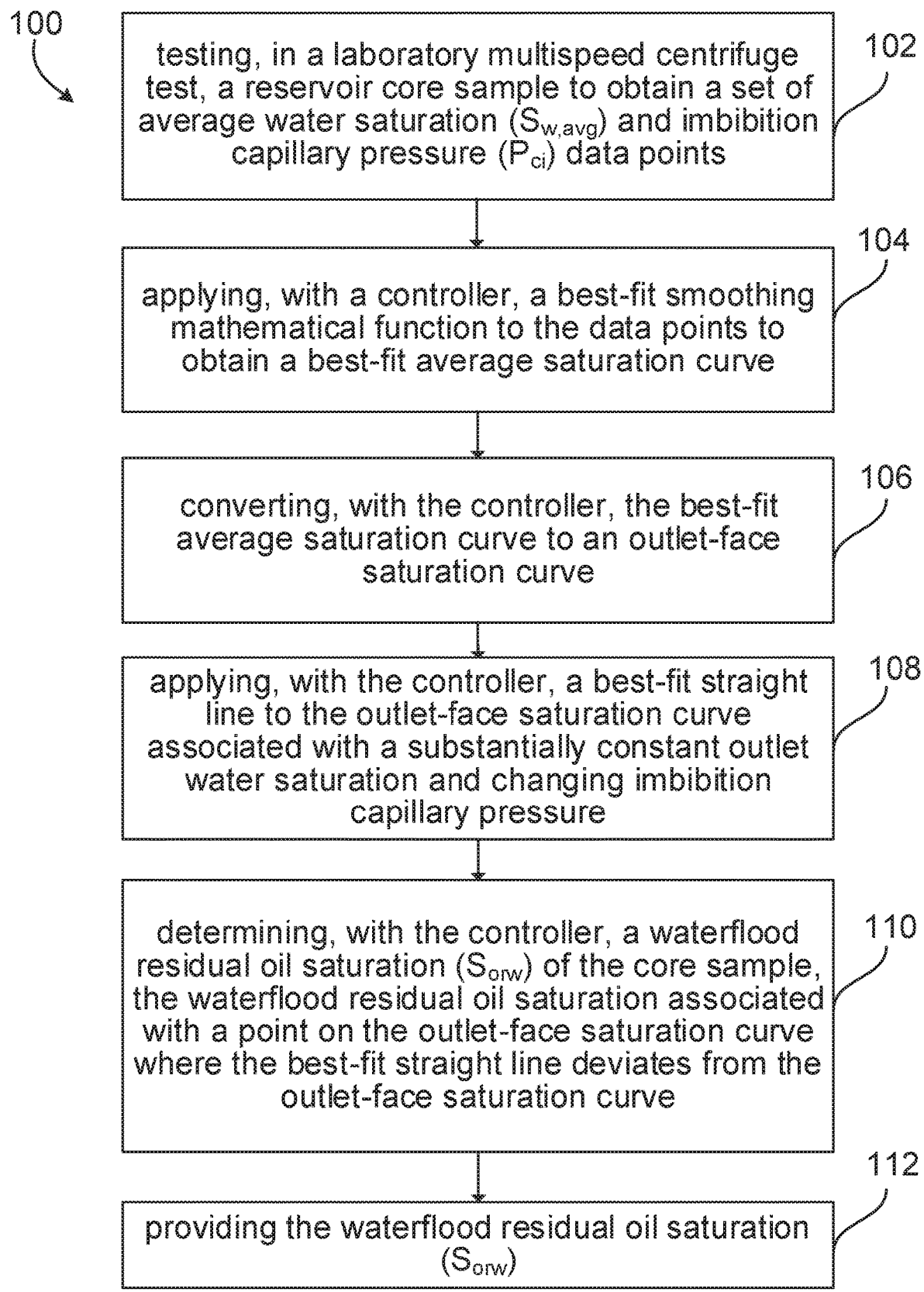
FIG. 1 is a flowchart of an example method for determining waterflood residual oil saturation of a reservoir core sample.

This disclosure describes testing a core sample, such as a reservoir core sample from a reservoir, to determine saturation characteristics of the core sample. A reservoir core sample is tested in a multispeed centrifuge test of water displacing oil, and the test data is interpreted and analyzed to determine an ultimate waterflood residual oil saturation ($S_{orw}$) of the core sample. The ultimate waterflood residual oil saturation represents the ratio of the volume of the oil trapped in pores of a rock under waterflooding to the total volume of the pores of the rock. For example, manipulating and interpreting a negative imbibition capillary pressure ($P_{ci}$) curve obtained from a laboratory multispeed centrifuge test of a reservoir core sample can lead to a determination of $S_{orw}$ for the reservoir core sample, which is representative of the $S_{orw}$ for oil reservoirs under waterflood from which the core sample was retrieved. In some subterranean wells, waterflooding includes injecting water into a reservoir or oil field to increase pressure, stimulate production, or both, through a production wellbore accessing the reservoir. The determined $S_{orw}$ from the testing and analysis of the reservoir core sample can be used to simulate the reservoir for assessing the ultimate recovery of the reservoir. For example, $S_{orw}$ can denote the endpoint on relative permeability curves as input for reservoir simulations. These determinations can affect drilling operations or production operations, or both, of subterranean wells. The determined $S_{orw}$, reservoir properties, reservoir simulation, ultimate recovery assessment, or a combination of these can directly or indirectly affect drilling or production activities in the field. $S_{orw}$ is a direct input into reservoir simulation which determines the productivity of wells/fields and this impacts operations, drilling, surface/subsurface facility/equipment, life of a field, economic returns, and field abandonment.

Wettability is a preference of a material (such as rock, or a reservoir rock sample) to one fluid with the presence of other fluids, for example, rock's wettability to oil with respect to water. How oil or water wets the rock controls the saturations and imbibition capillary pressure ($P_{ci}$) of these fluids within the rock. For example, if rock is water-wet, then the negative $P_{ci}$ covers a narrow range of water saturation; if rock is oil-wet, then the negative $P_{ci}$ covers a broad range of water saturation while an intermediate-wettability yields a negative $P_{ci}$ between the two. The present disclosure is applicable to reservoir core samples for any wettability.

Current industry practice of determination of waterflood residual oil saturation of a sample is often improperly and inadequately analyzed. For example, some centrifuge testing of samples interpret raw data from centrifuge tests using drainage analyses and equations, which is not accurate to an imbibition analysis of a core sample under waterflooding.

Other examples include the use of a non-unique, un-consensus capillary pressure end-point to determine residual oil saturation. This disclosure describes centrifuge testing of a sample, where the raw data from the centrifuge test is interpreted using imbibition analyses to properly associate the raw centrifuge test data to imbibition capillary pressure ($P_{ci}$). can be implementable using a computer-implemented method, a computer-readable medium (transitory or non-transitory) storing computer-readable instructions to perform the computer-implemented method, a computer system including a computer memory interoperably coupled with a hardware processor configured to perform the computer-implemented method/the instructions stored on the computer-readable medium, or other implementations.

Figure 2A:
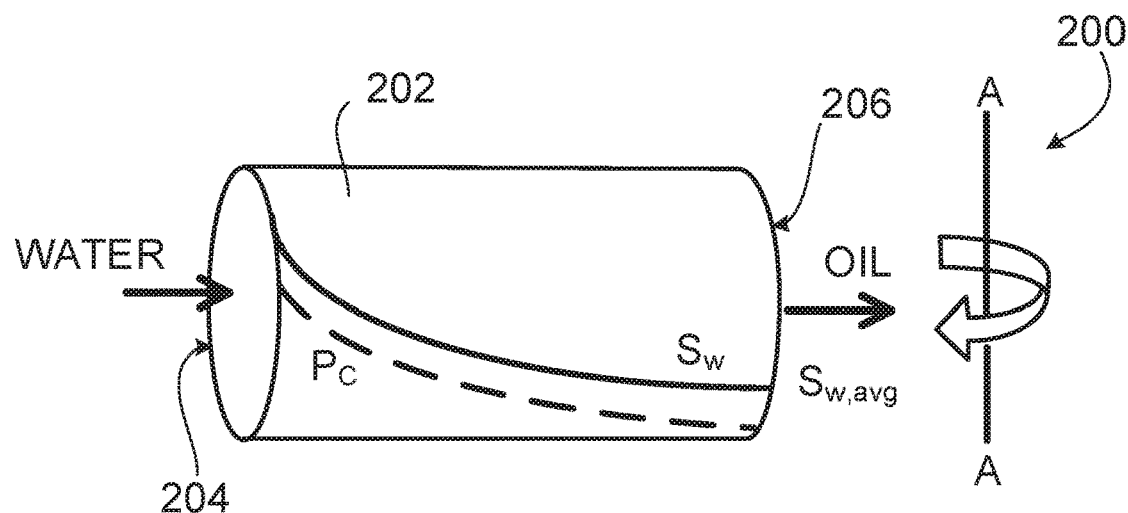
FIG. 2A is a schematic diagram of an example imbibition centrifuge test system.

FIG. 1 is a flowchart of an example method 100 for determining waterflood residual oil saturation ($S_{orw}$) of a sample, such as a reservoir core sample. The reservoir core sample can be a substantially cylindrical rock sample, such as a one-inch diameter and length cylindrical rock sample extracted from a subterranean reservoir. However, the size and shape of the reservoir core sample can vary. At 102, the reservoir core sample is tested in a laboratory multispeed centrifuge test to obtain a set of (for example, plurality of or multiple) average water saturation ($S_{w,avg}$) and imbibition capillary pressure ($P_{ci}$) data points. The laboratory multispeed centrifuge test includes an imbibition test of water displacing oil of the core sample. For example, FIG. 2A is a schematic diagram of an example imbibition centrifuge test system 200, where the core sample 202 is shown as having a cylindrical shape and oriented relative to a rotational axis A-A of the centrifuge test system 200. An inlet end 204 of the core sample 202, oriented farthest from the rotational axis, acts as an inlet surface for insertion of water for imbibition testing of the core sample 202, representing waterflooding of the core sample 202. An outlet end 206 of the core sample 202, oriented closest to the rotational axis A-A and opposite the inlet end 204, is the outlet for oil displaced by the water introduced at the inlet end 204.

In some implementations, testing the reservoir core sample 202 includes saturating the reservoir core sample 202 with connate formation water and dead crude oil, and placing the reservoir core sample 202 in an imbibition bucket of a centrifuge of the imbibition centrifuge test system 200. The imbibition bucket is filled, partially or completely, with injection water that enters into the inlet end 204 of the core sample 202 due to the fluid density differential during testing (for example, during rotation of the centrifuge) and pushes the oil out of the reservoir core sample at the outlet end 206. The fluid density of water is greater than the fluid density of oil, creating the fluid density differential. As water enters the core sample 202, pressure is highest at the innermost end near the outlet end 206 of the core sample 202, so the water pushes oil out of the reservoir core sample 202 out of the outlet end 206. The force of the water acting to push the oil toward the outlet end 206 is greater than the centrifugal force acting on the oil in an opposite, pulling direction toward the inlet end 204. A temperature in the imbibition bucket is set to a threshold temperature, for example, up to 90 degrees Celsius, or a threshold reservoir temperature simulating a temperature in the reservoir from which the core sample 202 was extracted. Further, the reservoir core sample 202 is rotated about the rotational axis A-A at multiple speeds, starting from low-to-high rotational speed that represents the range of reservoir pressure differential during field operation and production. A first rotational speed (for example, 200 rpm or other low rotational speed) is maintained until no more oil production from the reservoir core sample 202 is observed at the outlet end 206, then the rotational speed is increased to a next level. In some examples of the test, oil production from the reservoir core sample 202 is measured as the volume of oil exiting the outlet end 206 of the core sample 202, for example, measured in milliliters (mL).

The reservoir core sample 202 can be further rotated about the rotational axis A-A at a second rotational speed that is higher than the first rotational speed until no oil production from the reservoir core sample 202 is observed. The rotational speed of the centrifuge can be consecutively increased in a stepped manner, where the rotational speed is maintained at each stepped rotational speed until no oil production from the core sample 202 is observed. The rotational speed is then increased to the next stepped value. This stepped increase is maintained until oil production ceases from the reservoir core sample 202. Increasing the rotational speed applies more pressure on the water to enter the core sample, thereby pushing more oil out of the core sample. In some examples, the imbibition centrifuge test can be run at 10 or more rotational speeds, where the rotational speed and volume of oil production (output) are recorded.

In some implementations, testing the reservoir core sample to obtain the multiple $S_{w,avg}$ and $P_{ci}$ data points includes determining average water saturation ($S_{w,avg}$) data points from the measured volumes of expelled oil from the reservoir core sample 202 for multiple rotational speeds of the centrifuge test, and determining $P_{ci}$ using equation 1.

$$P_{ci} = \frac{1}{2}\Delta\rho\omega^2(r_3^2 - r_1^2) \qquad [1]$$

In Equation 1, $\Delta\rho$ is a density difference between oil and water, $\omega$ is a rotational speed of the centrifuge of the centrifuge test, $r_3$ is a distance between the inlet end 204 of the reservoir core sample 202 and the rotational axis A-A of the centrifuge, and $r_1$ is the distance between the 206 outlet end of the reservoir core sample 202 and the rotational axis A-A of the centrifuge. The centrifuge test results in multiple $P_{ci}$ values at least because the test is run at multiple speeds, resulting in multiple $P_{ci}$ values from Equation 1. The first measured volume of expelled oil at the first speed gives a value for a volume of water that has entered into the reservoir core sample for that speed. This volume is then converted to water saturation by dividing it by the total volume of the pores in the core sample. The converted water saturation is added to initial water saturation to determine average water saturation of the core sample ($S_{w,avg}$). The subsequent value of $S_{w,avg}$ is determined by adding the incremental change in water saturation in the core sample for each speed to $S_{w,avg,\ previous\ speed}$ (the average water saturation at a prior, lesser speed during centrifuge testing).

Figure 2B:
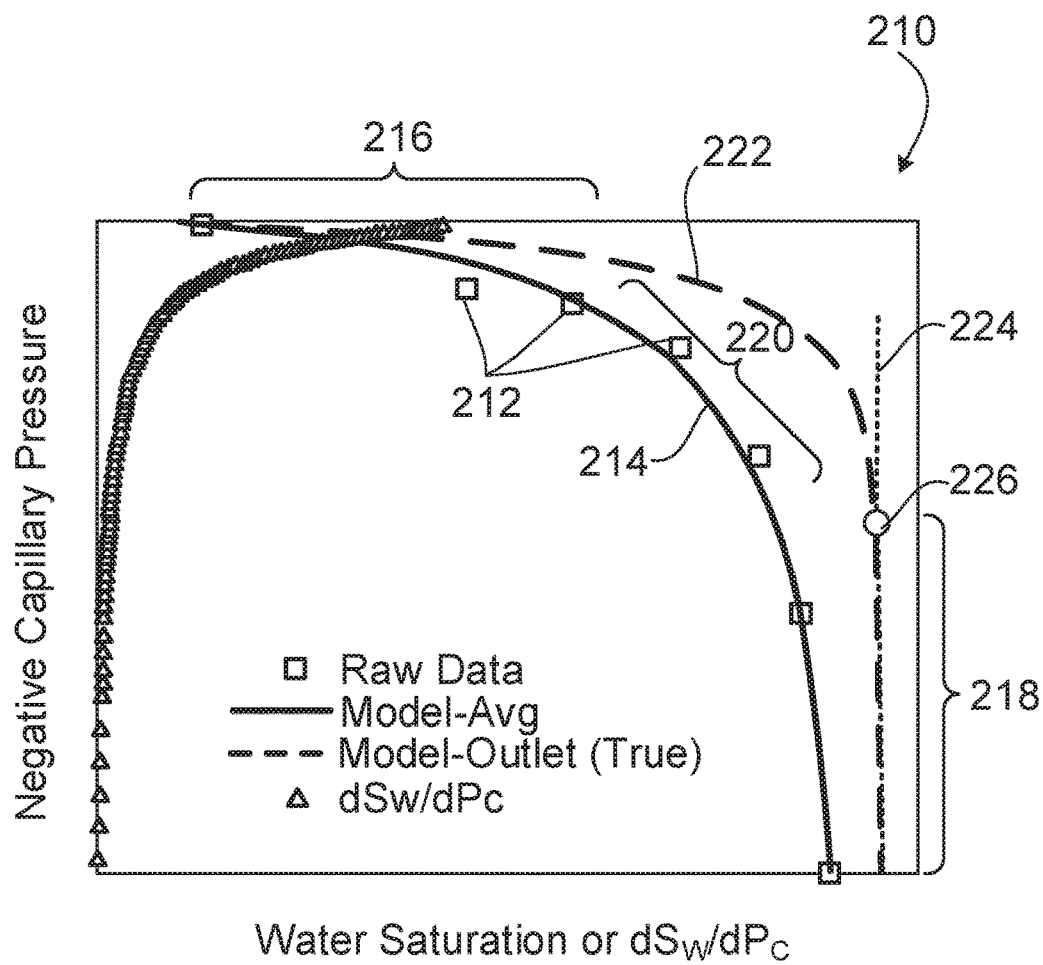
FIG. 2B is a plot of negative capillary pressure over water saturation showing example raw data obtained from an imbibition centrifuge test and showing an example best-fit average saturation curve and an example outlet-face saturation curve.

Referring back to FIG. 1, at 104, a controller, or engineer, applies a best-fit smoothing function to the data points to obtain a best-fit average saturation curve, where the best-fit average saturation curve represents imbibition capillary pressure ($P_{ci}$) over average water saturation ($S_{w,avg}$). Applying the best-fit smoothing function to the data points can include empirical matching, for example, applying a non-linear regression to the data points to obtain the best-fit average saturation curve, a trial-and-error modification, a combination of these, or another type of analysis to minimize error between the data and the model. In some implementations, applying the best-fit smoothing function to the data points includes plotting the following equation, Equation 2, for average water saturation ($S_{w,avg}$).

$$S_{w,avg} = 1 - a + \frac{1}{P_{ci}}\{b[1 - \exp(cP_{ci})] + d[1 - \exp(eP_{ci})]\} \quad [2]$$

a, b, c, d, and e are best-fit matching parameters. Parameters a and b affect a high-$P_{ci}$ section of the best-fit average saturation curve, parameters d and e affect a low-$P_{ci}$ section of the best-fit average saturation curve, and parameter c affects a transition section of the best-fit average saturation curve between the high-$P_{ci}$ section and the low-$P_{ci}$ section. For example, FIG. 2B is a plot 210 of negative imbibition capillary pressure (for example, $P_{ci}$ from Equation 1) over water saturation (for example, $S_w$, or $S_{w,avg}$ from Equation 2) showing example raw data 212 obtained from the imbibition centrifuge test of step 102, and showing an example best-fit average saturation curve 214. The best-fit average saturation curve 214 of FIG. 2B includes the low-$P_{ci}$ section 216, the high-$P_{ci}$ section 218, and the transition section 220 described earlier. FIG. 2B also shows the first derivative of water saturation with respect to capillary pressure ($dS_w/dP_c$).

Referring to both FIGS. 1 and 2B, at 106, the controller or engineer converts the best-fit average saturation curve 214 to an outlet-face saturation curve 222, where the outlet-face saturation curve 222 represents imbibition capillary pressure ($P_{ci}$) over outlet water saturation ($S_{w,avg}$). In some implementations, converting the best-fit average saturation curve 214 to the outlet-face saturation curve 222 includes plotting the following equation, equation 3, for outlet water saturation ($S_{w,outlet}$).

$$S_{w,outlet} = S_{w,avg} + P_{ci} \times \frac{dS_{w,avg}}{dP_{ci}} \quad [3]$$

$dS_{w,avg}/dP_{ci}$ is the derivative of the equation for average water saturation ($S_{w,avg}$). Plotting the equation for outlet water saturation ($S_{w,outlet}$) provides a true laboratory negative imbibition capillary pressure ($P_{ci}$) curve, for example, exemplified by the outlet-face saturation curve 222 of FIG. 2B.

At 108, the controller or engineer applies a best-fit straight line 224 to the outlet-face saturation curve 222 associated with a substantially constant outlet water saturation and changing imbibition capillary pressure. The best-fit straight line 224 is matched to a straight line portion of the outlet-face saturation curve, for example, in the high-$P_{ci}$ section 218. The best-fit straight line 224 is a near vertical line on the plot 210 corresponding to a substantially constant water saturation.

At 110, the controller or engineer determines a waterflood residual oil saturation ($S_{orw}$) of the core sample. The waterflood residual oil saturation is associated with a point 226 on the outlet-face saturation curve 222 where the best-fit straight line 224 deviates from the outlet-face saturation curve 222. The waterflood residual oil saturation ($S_{orw}$) represents the ratio of the volume of the oil trapped in pores of the reservoir core sample under waterflooding to the total volume of the pores of the reservoir core sample. In some implementations, determining the waterflood residual oil saturation ($S_{orw}$) of the core sample includes identifying the point 226 on the outlet-face saturation curve 222 corresponding to $dS_{w,avg}/dP_{ci}$ being equal to (approximately or exactly) 0.01. The waterflood residual oil saturation, or $S_{orw}$, of the core sample is a fraction or percent value used as the endpoint of relative permeability, which can be used as an input for reservoir simulation.

At 112, the waterflood residual oil saturation ($S_{orw}$) is provided. In some instances, a display device connected to the controller displays the waterflood residual oil saturation ($S_{orw}$). The determined $S_{orw}$ is a direct input into reservoir simulation which can drive, alter, or otherwise affect the productivity of wells/fields and impacts operations, drilling, surface/subsurface facility/equipment, life of a field, economic returns, and field abandonment. For example, the determined $S_{orw}$ can drive, alter, or otherwise affect drilling or production operations. Also, the determined $S_{orw}$ plays a significant role in reserves estimation of hydrocarbons. For example, upon realizing the residual oil saturation ($S_{or}$), the following activities can be executed to determine the reserves or the number of barrels of hydrocarbon that can be recovered at the end of the waterflood: normalize the relative permeability (Kr) curves to the $S_{or}$ value(s), Feed the Kr curves to reservoir simulation models, and/or run the model to the field/reservoir abandonment to determine how much cumulatively the reservoir has been able to produce up to abandonment, where the cumulative production is the reserves of the reservoir which is used to determine the market value of the oil.

Figure 3:
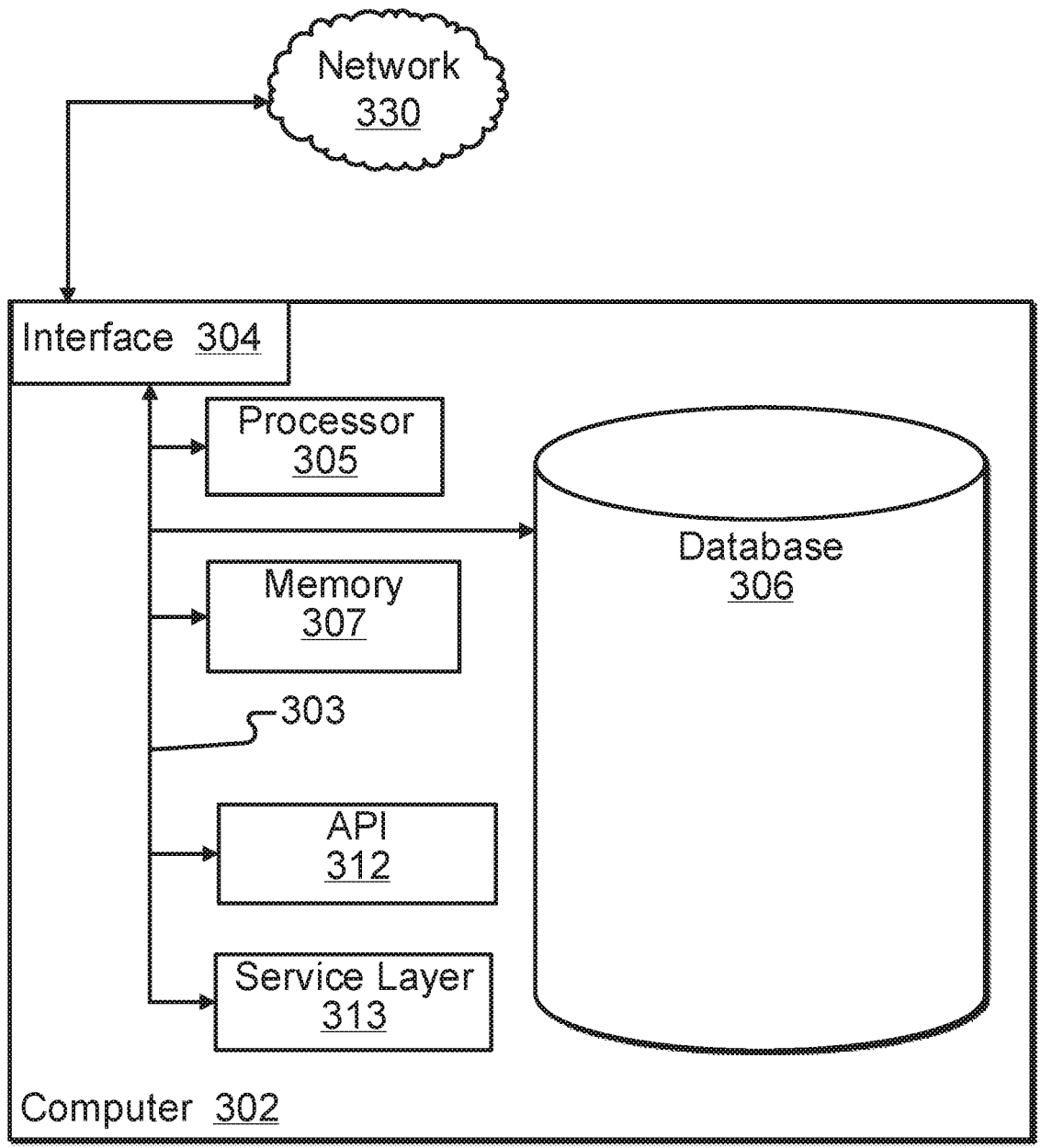
FIG. 3 is a block diagram of an example computer system used to provide computational functionalities associated with described algorithms, functions, processes, flows, and procedures as described in the instant disclosure, according to an implementation.

FIG. 3 is a schematic view of an example computer system 300. In particular, FIG. 3 is a block diagram of the example computer system 300 used to provide computational functionalities associated with described algorithms, methods, functions, processes, flows, and procedures as described in the instant disclosure, according to an implementation. The illustrated computer 302 is intended to encompass any computing device such as a server, desktop computer, laptop/notebook computer, wireless data port, smart phone, personal data assistant (PDA), tablet computing device, one or more controllers or processors within these devices, or any other suitable processing device, including both physical or virtual instances (or both) of the computing device. Additionally, the computer 302 may comprise a computer that includes an input device, such as a keypad, keyboard, touch screen, or other device that can accept user information, and an output device (for example, a display device, such as a screen) that conveys information associated with the operation of the computer 302, including digital data, visual, or audio information (or a combination of information), or a graphical user interface (GUI).

The computer 302 can serve in a role as a client, network component, a server, a database or other persistency, or any other component (or a combination of roles) of a computer system for performing the subject matter described in the instant disclosure. The illustrated computer 302 can be communicably coupled with a network 330. In some implementations, one or more components of the computer 302 may be configured to operate within environments, including cloud-computing-based, local, global, or other environment (or a combination of environments).

At a high level, the computer 302 is an electronic computing device operable to receive, transmit, process, store, or manage data and information associated with the described subject matter. Each of the components of the computer 302 can communicate using a system bus 303. In some implementations, any or all of the components of the computer 302, both hardware or software (or a combination of hardware and software), may interface with each other or the interface 304 (or a combination of both) over the system bus 303 using an application programming interface (API) 312 or a service layer 313 (or a combination of the API 312 and service layer 313). The service layer 313 provides software services to the computer 302 or other components (whether or not illustrated) that are communicably coupled to the computer 302.

The computer 302 includes an interface 304. Although illustrated as a single interface 304 in FIG. 3, two or more interfaces 304 may be used according to particular needs, desires, or particular implementations of the computer 302. The interface 304 is used by the computer 302 for communicating with other systems in a distributed environment that are connected to the network 330 (whether illustrated or not). Generally, the interface 304 comprises logic encoded in software or hardware (or a combination of software and hardware) and operable to communicate with the network 330. More specifically, the interface 304 may comprise software supporting one or more communication protocols associated with communications such that the network 330 or interface's hardware is operable to communicate physical signals within and outside of the illustrated computer 302.

The computer 302 includes a controller, or processor 305. Although illustrated as a single processor 305 in FIG. 3, two or more processors may be used according to particular needs, desires, or particular implementations of the computer 302. Generally, the processor 305 executes instructions and manipulates data to perform the operations of the computer 302 and any algorithms, methods, functions, processes, flows, and procedures as described in the instant disclosure.

The computer 302 also includes a database 306 that can hold data for the computer 302 or other components (or a combination of both) that can be connected to the network 330 (whether illustrated or not). For example, database 306 can be an in-memory, conventional, or other type of database storing data consistent with this disclosure. In some implementations, database 306 can be a combination of two or more different database types (for example, a hybrid in-memory and conventional database) according to particular needs, desires, or particular implementations of the computer 302 and the described functionality. Although illustrated as a single database 306 in FIG. 3, two or more databases (of the same or combination of types) can be used according to particular needs, desires, or particular implementations of the computer 302 and the described functionality. While database 306 is illustrated as an integral component of the computer 302, in alternative implementations, database 306 can be external to the computer 302.

The computer 302 also includes a memory 307 that can hold data for the computer 302 or other components (or a combination of both) that can be connected to the network 330 (whether illustrated or not). For example, memory 307 can be random access memory (RAM), read-only memory (ROM), optical, magnetic, and the like storing data consistent with this disclosure. In some implementations, memory 307 can be a combination of two or more different types of memory (for example, a combination of RAM and magnetic storage) according to particular needs, desires, or particular implementations of the computer 302 and the described functionality. Although illustrated as a single memory 307 in FIG. 3, two or more memories 307 (of the same or combination of types) can be used according to particular needs, desires, or particular implementations of the computer 302 and the described functionality. While memory 307 is illustrated as an integral component of the computer 302, in alternative implementations, memory 307 can be external to the computer 302. There may be any number of computers 302 associated with, or external to, a computer system containing computer 302, each computer 302 communicating over network 330.

Figure 4:
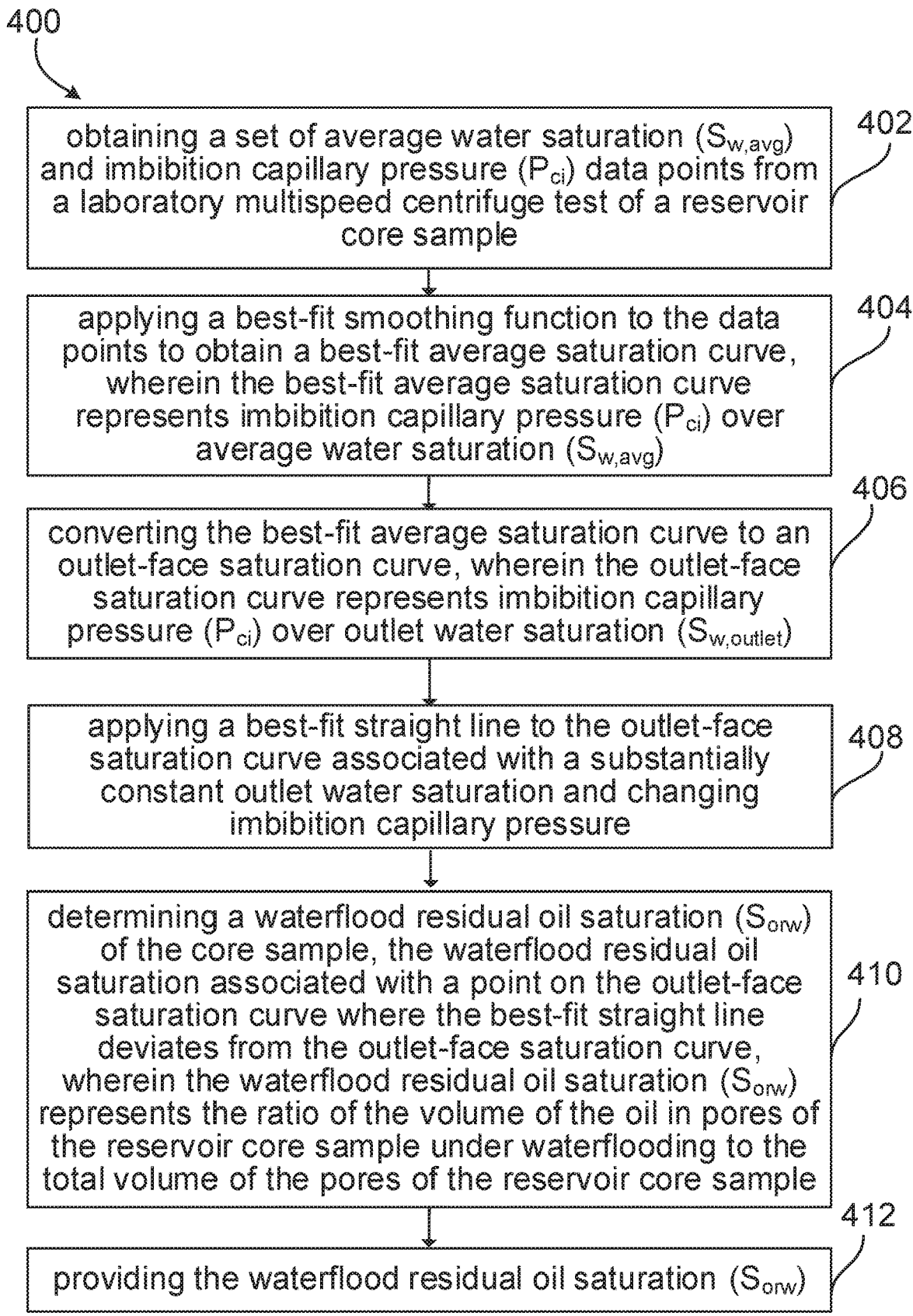
FIG. 4 is a flowchart of an example computer-implemented method of analyzing a reservoir core sample tested under a laboratory multispeed centrifuge test of water displacing oil.

FIG. 4 is a flowchart of an example computer-implemented method 400 of analyzing a reservoir core sample tested under a laboratory multispeed centrifuge test of water displacing oil, for example, performed by the example computer system 300 of FIG. 3. At 402, a set, or plurality, of average water saturation ($S_{w,avg}$) and imbibition capillary pressure ($P_{ci}$) data points are obtained from a laboratory multispeed centrifuge test of a reservoir core sample. At 404, a controller applies a best-fit smoothing function to the data points to obtain a best-fit average saturation curve, where the best-fit average saturation curve represents imbibition capillary pressure ($P_{ci}$) over average water saturation ($S_{w,avg}$). At 406, the controller converts the best-fit average saturation curve to an outlet-face saturation curve, wherein the outlet-face saturation curve represents imbibition capillary pressure ($P_{ci}$) over outlet water saturation ($S_{w,outlet}$). At 408, the controller applies a best-fit straight line to the outlet-face saturation curve associated with a substantially constant outlet water saturation and changing imbibition capillary pressure. At 410, the controller determines a waterflood residual oil saturation ($S_{orw}$) of the core sample, the waterflood residual oil saturation associated with a point on the outlet-face saturation curve where the best-fit straight line deviates from the outlet-face saturation curve, where the waterflood residual oil saturation ($S_{orw}$) represents the ratio of the volume of the oil in pores of the reservoir core sample under waterflooding to the total volume of the pores of the reservoir core sample. At 412, the waterflood residual oil saturation ($S_{orw}$) is provided.

In some aspects, a method of determining waterflood residual oil saturation comprises testing, in a laboratory multispeed centrifuge test, a reservoir core sample to obtain a set of average water saturation ($S_{w,avg}$) and imbibition capillary pressure ($P_{ci}$) data points, applying, with a controller, a best-fit smoothing function to the data points to obtain a best-fit average saturation curve, wherein the best-fit average saturation curve represents imbibition capillary pressure (PO over average water saturation ($S_{w,avg}$), and converting, with the controller, the best-fit average saturation curve to an outlet-face saturation curve, wherein the outlet-face saturation curve represents imbibition capillary pressure ($P_{ci}$) over outlet water saturation ($S_{w,outlet}$). The method further comprises applying, with the controller, a best-fit straight line to the outlet-face saturation curve associated with a substantially constant outlet water saturation and changing imbibition capillary pressure, determining, with the controller, a waterflood residual oil saturation ($S_{orw}$) of the core sample, the waterflood residual oil saturation associated with a point on the outlet-face saturation curve where the best-fit straight line deviates from the outlet-face saturation curve, wherein the waterflood residual oil saturation ($S_{orw}$) represents the ratio of the volume of the oil trapped in pores of the reservoir core sample under waterflooding to the total volume of the pores of the reservoir core sample, and providing the waterflood residual oil saturation ($S_{orw}$).

In an aspect combinable with any other aspect, testing the reservoir core sample to obtain a set of average water saturation ($S_{w,avg}$) and imbibition capillary pressure ($P_{ci}$) data points comprises determining average water saturation ($S_{w,avg}$) data points from measured volumes of expelled oil from the reservoir core sample for a set of rotational speeds of the centrifuge test, and determining imbibition capillary pressure ($P_{ci}$) using the following equation:

$$P_{ci} = \frac{1}{2}\Delta\rho\omega^2(r_3^2 - r_1^2);$$

where $\Delta\rho$ is a density difference between oil and water, $\omega$ is a rotational speed of the centrifuge of the centrifuge test, $r_3$ is a distance between an inlet end of the reservoir core sample and a rotational axis of the centrifuge, $r_1$ is the distance between an outlet end of the reservoir core sample and the rotational axis of the centrifuge.

In another aspect combinable with any other aspect, testing the reservoir core sample to obtain a set of water saturation ($S_{w,avg}$) and imbibition capillary pressure ($P_{ci}$) data points comprises saturating the reservoir core sample with connate formation water and dead crude oil, placing the reservoir core sample in an imbibition bucket of the centrifuge, the imbibition bucket being at least partially filled with injection water, setting a temperature in the imbibition bucket to a threshold reservoir temperature, rotating the reservoir core sample at a first rotational speed until no oil production from the reservoir core sample is observed, and rotating the reservoir core sample at a second rotational speed higher than the first rotational speed until no oil production from the reservoir core sample is observed.

In another aspect combinable with any other aspect, applying a best-fit smoothing function to the data points to obtain a best-fit average saturation curve comprises plotting the following equation for average water saturation ($S_{w,avg}$):

$$S_{w,avg} = 1 - a + \frac{1}{P_{ci}}\{b[1 - \exp(cP_{ci})] + d[1 - \exp(eP_{ci})]\};$$

where a, b, c, d, and e are best-fit matching parameters, and wherein parameters a and b affect a high-$P_{ci}$ section of the best-fit average saturation curve, parameters d and e affect a low-$P_{ci}$ section of the best-fit average saturation curve, and parameter c affects a transition section of the best-fit average saturation curve between the high-$P_{ci}$ section and the low-$P_{ci}$ section.

In another aspect combinable with any other aspect, applying a best-fit smoothing function to the data points to obtain the best-fit average saturation curve comprises applying a non-linear regression to the data points to obtain the best-fit average saturation curve.

In another aspect combinable with any other aspect, converting the best-fit average saturation curve to the outlet-face saturation curve comprises plotting the following equation for outlet water saturation $$S_{w,outlet} = S_{w,avg} + P_{ci} \times \frac{dS_{w,avg}}{dP_{ci}};$$

where $dS_{w,avg}/dP_{ci}$ is the derivative of the equation for average water saturation ($S_{w,avg}$), wherein plotting the equation for outlet water saturation ($S_{w,outlet}$) provides a true laboratory negative imbibition capillary pressure ($P_{ci}$) curve.

In another aspect combinable with any other aspect, determining the waterflood residual oil saturation ($S_{orw}$) of the core sample, where the waterflood residual oil saturation is associated with a point on the outlet-face saturation curve where the best-fit straight line deviates from the outlet-face saturation curve, comprises identifying the point on the outlet-face saturation curve corresponding to $dS_{w,avg}/dP_{ci}$ being equal to approximately 0.01.

In another aspect combinable with any other aspect, the laboratory multispeed centrifuge test on the reservoir core sample comprises an imbibition test of water displacing oil.

In another aspect combinable with any other aspect, providing the waterflood residual oil saturation ($S_{orw}$) comprises displaying the waterflood residual oil saturation ($S_{orw}$) in a display of a display device connected to the controller.

In some aspects, a computer-implemented method of analyzing a reservoir core sample tested under a laboratory multispeed centrifuge test of water displacing oil comprises obtaining a set of average water saturation ($S_{w,avg}$) and imbibition capillary pressure ($P_{ci}$) data points from a laboratory multispeed centrifuge test of a reservoir core sample, applying, with a controller, a best-fit smoothing function to the data points to obtain a best-fit average saturation curve, wherein the best-fit average saturation curve represents imbibition capillary pressure ($P_{ci}$) over average water saturation ($S_{w,avg}$), converting, with the controller, the best-fit average saturation curve to an outlet-face saturation curve, wherein the outlet-face saturation curve represents imbibition capillary pressure ($P_{ci}$) over outlet water saturation ($S_{w,outlet}$), applying, with the controller, a best-fit straight line to the outlet-face saturation curve associated with a substantially constant outlet water saturation and changing imbibition capillary pressure, determining, with the controller, a waterflood residual oil saturation ($S_{orw}$) of the core sample, the waterflood residual oil saturation associated with a point on the outlet-face saturation curve where the best-fit straight line deviates from the outlet-face saturation curve, wherein the waterflood residual oil saturation ($S_{orw}$) represents the ratio of the volume of the oil trapped in pores of the reservoir core sample under waterflooding to the total volume of the pores of the reservoir core sample, and providing the waterflood residual oil saturation ($S_{orw}$).

In another aspect combinable with any other aspect, testing the reservoir core sample to obtain a set of average water saturation ($S_{w,avg}$) and imbibition capillary pressure ($P_{ci}$) data points comprises determining average water saturation ($S_{w,avg}$) data points from measured volumes of expelled oil from the reservoir core sample for a set of rotational speeds of the centrifuge test, and determining imbibition capillary pressure ($P_{ci}$) using the following equation:

$$P_{ci} = \frac{1}{2}\Delta\rho\omega^2(r_3^2 - r_1^2);$$

where $\Delta\rho$ is a density difference between oil and water, $\omega$ is a rotational speed of the centrifuge of the centrifuge test, $r_3$ is a distance between an inlet end of the reservoir core sample and a rotational axis of the centrifuge, $r_1$ is the distance between an outlet end of the reservoir core sample and the rotational axis of the centrifuge.

In another aspect combinable with any other aspect, applying a best-fit smoothing function to the data points to obtain a best-fit average saturation curve comprises plotting the following equation for average water saturation ($S_{w,avg}$):

$$S_{w,avg} = 1 - a + \frac{1}{P_{ci}}\{b[1 - \exp(cP_{ci})] + d[1 - \exp(eP_{ci})]\};$$

where a, b, c, d, and e are best-fit matching parameters, and wherein parameters a and b affect a high-$P_{ci}$ section of the best-fit average saturation curve, parameters d and e affect a low-$P_{ci}$ section of the best-fit average saturation curve, and parameter c affects a transition section of the best-fit average saturation curve between the high-$P_{ci}$ section and the low-$P_{ci}$ section.

In another aspect combinable with any other aspect, applying a best-fit smoothing function to the data points to obtain the best-fit average saturation curve comprises applying a non-linear regression to the data points to obtain the best-fit average saturation curve.

In another aspect combinable with any other aspect, converting the best-fit average saturation curve to the outlet-face saturation curve comprises plotting the following equation for outlet water saturation $$S_{w,outlet} = S_{w,avg} + P_{ci} \times \frac{dS_{w,avg}}{dP_{ci}};$$

where $dS_{w,avg}/dP_{ci}$ is the derivative of the equation for average water saturation ($S_{w,avg}$), wherein plotting the equation for outlet water saturation ($S_{w,outlet}$) provides a true laboratory negative imbibition capillary pressure ($P_{ci}$) curve.

In another aspect combinable with any other aspect, determining the waterflood residual oil saturation ($S_{orw}$) of the core sample, where the waterflood residual oil saturation is associated with a point on the outlet-face saturation curve where the best-fit straight line deviates from the outlet-face saturation curve, comprises identifying the point on the outlet-face saturation curve corresponding to $dS_{w,avg}/dP_{ci}$ being equal to approximately 0.01.

In another aspect combinable with any other aspect, providing the waterflood residual oil saturation ($S_{orw}$) comprises displaying the waterflood residual oil saturation ($S_{orw}$) in a display of a display device connected to the controller.

In some aspects, a computer-readable medium storing instructions operable when executed by one or more processors to perform operations comprises obtaining a set of average water saturation ($S_{w,avg}$) and imbibition capillary pressure ($P_{ci}$) data points from a laboratory multispeed centrifuge test of a reservoir core sample, applying a best-fit smoothing function to the data points to obtain a best-fit average saturation curve, wherein the best-fit average saturation curve represents imbibition capillary pressure ($P_{ci}$) over average water saturation ($S_{w,avg}$), converting the best-fit average saturation curve to an outlet-face saturation curve, wherein the outlet-face saturation curve represents imbibition capillary pressure ($P_{ci}$) over outlet water saturation ($S_{w,outlet}$), applying a best-fit straight line to the outlet-face saturation curve associated with a substantially constant outlet water saturation and changing imbibition capillary pressure, determining a waterflood residual oil saturation ($S_{orw}$) of the core sample, the waterflood residual oil saturation associated with a point on the outlet-face saturation curve where the best-fit straight line deviates from the outlet-face saturation curve, wherein the waterflood residual oil saturation ($S_{orw}$) represents the ratio of the volume of the oil trapped in pores of the reservoir core sample under waterflooding to the total volume of the pores of the reservoir core sample, and providing the waterflood residual oil saturation ($S_{orw}$).

In another aspect combinable with any other aspect, testing the reservoir core sample to obtain a set of average water saturation ($S_{w,avg}$) and imbibition capillary pressure ($P_{ci}$) data points comprises determining average water saturation ($S_{w,avg}$) data points from measured volumes of expelled oil from the reservoir core sample for a set of rotational speeds of the centrifuge test, and determining imbibition capillary pressure ($P_{ci}$) using the following equation:

$$P_{ci} = \frac{1}{2}\Delta\rho\omega^2(r_3^2 - r_1^2);$$

where $\Delta\rho$ is a density difference between oil and water, $\omega$ is a rotational speed of the centrifuge of the centrifuge test, $r_3$ is a distance between an inlet end of the reservoir core sample and a rotational axis of the centrifuge, $r_1$ is the distance between an outlet end of the reservoir core sample and the rotational axis of the centrifuge.

In another aspect combinable with any other aspect, applying a best-fit smoothing function to the data points to obtain a best-fit average saturation curve comprises plotting the following equation for average water saturation ($S_{w,avg}$):

$$S_{w,avg} = 1 - a + \frac{1}{P_{ci}}\{b[1 - \exp(cP_{ci})] + d[1 - \exp(eP_{ci})]\};$$

where a, b, c, d, and e are best-fit matching parameters, and wherein parameters a and b affect a high-$P_{ci}$ section of the best-fit average saturation curve, parameters d and e affect a low-$P_{ci}$ section of the best-fit average saturation curve, and parameter c affects a transition section of the best-fit average saturation curve between the high-$P_{ci}$ section and the low-$P_{ci}$ section.

In another aspect combinable with any other aspect, applying a best-fit smoothing function to the data points to obtain the best-fit average saturation curve comprises applying a non-linear regression to the data points to obtain the best-fit average saturation curve.

In another aspect combinable with any other aspect, converting the best-fit average saturation curve to the outlet-face saturation curve comprises plotting the following equation for outlet water saturation $$S_{w,outlet} = S_{w,avg} + P_{ci} \times \frac{dS_{w,avg}}{dP_{ci}};$$

where $dS_{w,avg}/dP_{ci}$ is the derivative of the equation for average water saturation ($S_{w,avg}$), wherein plotting the equation for outlet water saturation ($S_{w,outlet}$) provides a true laboratory negative imbibition capillary pressure ($P_{ci}$) curve.

In another aspect combinable with any other aspect, determining the waterflood residual oil saturation ($S_{orw}$) of the core sample, where the waterflood residual oil saturation is associated with a point on the outlet-face saturation curve where the best-fit straight line deviates from the outlet-face saturation curve, comprises identifying the point on the outlet-face saturation curve corresponding to $dS_{w,avg}/dP_{ci}$ being equal to approximately 0.01.

A number of implementations have been described. Nevertheless, it will be understood that various modifications may be made without departing from the spirit and scope of the disclosure.

What is claimed is:

1. A method of determining waterflood residual oil saturation, the method comprising:

testing, in a laboratory multispeed centrifuge test, a reservoir core sample to obtain a set of average water saturation ($S_{w,avg}$) and imbibition capillary pressure ($P_{ci}$) data points;

applying, with a controller, a best-fit smoothing function to the data points to obtain a best-fit average saturation curve, wherein the best-fit average saturation curve represents imbibition capillary pressure ($P_{ci}$) over average water saturation ($S_{w,avg}$);

converting, with the controller, the best-fit average saturation curve to an outlet-face saturation curve, wherein the outlet-face saturation curve represents imbibition capillary pressure ($P_{ci}$) over outlet water saturation ($S_{w,outlet}$);

applying, with the controller, a best-fit straight line to the outlet-face saturation curve associated with a substantially constant outlet water saturation and changing imbibition capillary pressure;

determining, with the controller, a waterflood residual oil saturation ($S_{orw}$) of the core sample, the waterflood residual oil saturation associated with a point on the outlet-face saturation curve where the best-fit straight line deviates from the outlet-face saturation curve, wherein the waterflood residual oil saturation ($S_{orw}$) represents the ratio of the volume of the oil trapped in pores of the reservoir core sample under waterflooding to the total volume of the pores of the reservoir core sample; and providing the waterflood residual oil saturation ($S_{orw}$).

2. The method of claim 1, wherein testing the reservoir core sample to obtain a set of average water saturation ($S_{w,avg}$) and imbibition capillary pressure ($P_{ci}$) data points comprises:

determining average water saturation ($S_{w,avg}$) data points from measured volumes of expelled oil from the reservoir core sample for a set of rotational speeds of the centrifuge test; and determining imbibition capillary pressure ($P_{ci}$) using the following equation:

$$P_{ci} = \frac{1}{2}\Delta\rho\omega^2(r_3^2 - r_1^2);$$

where $\Delta\rho$ is a density difference between oil and water, $\omega$ is a rotational speed of the centrifuge of the centrifuge test, $r_3$ is a distance between an inlet end of the reservoir core sample and a rotational axis of the centrifuge, $r_1$ is the distance between an outlet end of the reservoir core sample and the rotational axis of the centrifuge.

3. The method of claim 2, wherein testing the reservoir core sample to obtain a set of water saturation ($S_{w,avg}$) and imbibition capillary pressure ($P_{ci}$) data points comprises:

saturating the reservoir core sample with connate formation water and dead crude oil;

placing the reservoir core sample in an imbibition bucket of the centrifuge, the imbibition bucket being at least partially filled with injection water;

setting a temperature in the imbibition bucket to a threshold reservoir temperature;

rotating the reservoir core sample at a first rotational speed until no oil production from the reservoir core sample is observed; and rotating the reservoir core sample at a second rotational speed higher than the first rotational speed until no oil production from the reservoir core sample is observed.

4. The method of claim 1, wherein applying a best-fit smoothing function to the data points to obtain a best-fit average saturation curve comprises plotting the following equation for average water saturation ($S_{w,avg}$):

$$S_{w,avg} = 1 - a + \frac{1}{P_{ci}}\{b[1 - \exp(cP_{ci})] + d[1 - \exp(eP_{ci})]\};$$

where a, b, c, d, and e are best-fit matching parameters, and wherein parameters a and b affect a high-$P_{ci}$ section of the best-fit average saturation curve, parameters d and e affect a low-$P_{ci}$ section of the best-fit average saturation curve, and parameter c affects a transition section of the best-fit average saturation curve between the high-$P_{ci}$ section and the low-$P_{ci}$ section.

5. The method of claim 4, wherein applying a best-fit smoothing function to the data points to obtain the best-fit average saturation curve comprises applying a non-linear regression to the data points to obtain the best-fit average saturation curve.

6. The method of claim 4, wherein converting the best-fit average saturation curve to the outlet-face saturation curve comprises plotting the following equation for outlet water saturation ($S_{w,outlet}$):

$$S_{w,outlet} = S_{w,avg} + P_{ci} \times \frac{dS_{w,avg}}{dP_{ci}};$$

where $dS_{w,avg}/dP_{ci}$ is the derivative of the equation for average water saturation ($S_{w,avg}$), wherein plotting the equation for outlet water saturation ($S_{w,outlet}$) provides a true laboratory negative imbibition capillary pressure ($P_{ci}$) curve.

7. The method of claim 6, wherein determining the waterflood residual oil saturation ($S_{orw}$) of the core sample, where the waterflood residual oil saturation is associated with a point on the outlet-face saturation curve where the best-fit straight line deviates from the outlet-face saturation curve, comprises identifying the point on the outlet-face saturation curve corresponding to $dS_{w,avg}/dP_{ci}$ being equal to approximately 0.01.

8. The method of claim 1, wherein the laboratory multispeed centrifuge test on the reservoir core sample comprises an imbibition test of water displacing oil.

9. The method of claim 1, wherein providing the waterflood residual oil saturation ($S_{orw}$) comprises displaying the waterflood residual oil saturation ($S_{orw}$) in a display of a display device connected to the controller.

10. A computer-implemented method of analyzing a reservoir core sample tested under a laboratory multispeed centrifuge test of water displacing oil, the computer-implemented method comprising:

obtaining a set of average water saturation ($S_{w,avg}$) and imbibition capillary pressure ($P_{ci}$) data points from a laboratory multispeed centrifuge test of a reservoir core sample;

applying, with a controller, a best-fit smoothing function to the data points to obtain a best-fit average saturation curve, wherein the best-fit average saturation curve represents imbibition capillary pressure ($P_{ci}$) over average water saturation ($S_{w,avg}$);

converting, with the controller, the best-fit average saturation curve to an outlet-face saturation curve, wherein the outlet-face saturation curve represents imbibition capillary pressure ($P_{ci}$) over outlet water saturation ($S_{w,outlet}$);

applying, with the controller, a best-fit straight line to the outlet-face saturation curve associated with a substantially constant outlet water saturation and changing imbibition capillary pressure;

determining, with the controller, a waterflood residual oil saturation ($S_{orw}$) of the core sample, the waterflood residual oil saturation associated with a point on the outlet-face saturation curve where the best-fit straight line deviates from the outlet-face saturation curve, wherein the waterflood residual oil saturation ($S_{orw}$) represents the ratio of the volume of the oil trapped in pores of the reservoir core sample under waterflooding to the total volume of the pores of the reservoir core sample; and providing the waterflood residual oil saturation ($S_{orw}$).

11. The computer-implemented method of claim 10, wherein testing the reservoir core sample to obtain a set of average water saturation ($S_{w,avg}$) and imbibition capillary pressure ($P_{ci}$) data points comprises:

determining average water saturation ($S_{w,avg}$) data points from measured volumes of expelled oil from the reservoir core sample for a set of rotational speeds of the centrifuge test; and determining imbibition capillary pressure ($P_{ci}$) using the following equation:

$$P_{ci} = \frac{1}{2}\Delta\rho\omega^2(r_3^2 - r_1^2);$$

where $\Delta\rho$ is a density difference between oil and water, $\omega$ is a rotational speed of the centrifuge of the centrifuge test, $r_3$ is a distance between an inlet end of the reservoir core sample and a rotational axis of the centrifuge, $r_1$ is the distance between an outlet end of the reservoir core sample and the rotational axis of the centrifuge.

12. The computer-implemented method of claim 10, wherein applying a best-fit smoothing function to the data points to obtain a best-fit average saturation curve comprises plotting the following equation for average water saturation ($S_{w,avg}$):

$$S_{w,avg} = 1 - a + \frac{1}{P_{ci}}\{b[1 - \exp(cP_{ci})] + d[1 - \exp(eP_{ci})]\};$$

where a, b, c, d, and e are best-fit matching parameters, and wherein parameters a and b affect a high-$P_{ci}$ section of the best-fit average saturation curve, parameters d and e affect a low-$P_{ci}$ section of the best-fit average saturation curve, and parameter c affects a transition section of the best-fit average saturation curve between the high-$P_{ci}$ section and the low-$P_{ci}$ section.

13. The computer-implemented method of claim 12, wherein applying a best-fit smoothing function to the data points to obtain the best-fit average saturation curve comprises applying a non-linear regression to the data points to obtain the best-fit average saturation curve.

14. The computer-implemented method of claim 12, wherein converting the best-fit average saturation curve to the outlet-face saturation curve comprises plotting the following equation for outlet water saturation ($S_{w,outlet}$):

$$S_{w,outlet} = S_{w,avg} + P_{ci} \times \frac{dS_{w,avg}}{dP_{ci}};$$

where $dS_{w,avg}/dP_{ci}$ is the derivative of the equation for average water saturation ($S_{w,avg}$), wherein plotting the equation for outlet water saturation ($S_{w,outlet}$) provides a true laboratory negative imbibition capillary pressure ($P_{ci}$) curve.

15. The computer-implemented method of claim 14, wherein determining the waterflood residual oil saturation ($S_{orw}$) of the core sample, where the waterflood residual oil saturation is associated with a point on the outlet-face saturation curve where the best-fit straight line deviates from the outlet-face saturation curve, comprises identifying the point on the outlet-face saturation curve corresponding to $dS_{w,avg}/dP_{ci}$ being equal to approximately 0.01.

16. The method of claim 10, wherein providing the waterflood residual oil saturation ($S_{orw}$) comprises displaying the waterflood residual oil saturation ($S_{orw}$) in a display of a display device connected to the controller.

17. A computer-readable medium storing instructions operable when executed by one or more processors to perform operations comprising:

obtaining a set of average water saturation ($S_{w,avg}$) and imbibition capillary pressure ($P_{ci}$) data points from a laboratory multispeed centrifuge test of a reservoir core sample;

applying a best-fit smoothing function to the data points to obtain a best-fit average saturation curve, wherein the best-fit average saturation curve represents imbibition capillary pressure (Pc') over average water saturation ($S_{w,avg}$);

converting the best-fit average saturation curve to an outlet-face saturation curve, wherein the outlet-face saturation curve represents imbibition capillary pressure ($P_{ci}$) over outlet water saturation ($S_{w,outlet}$);

applying a best-fit straight line to the outlet-face saturation curve associated with a substantially constant outlet water saturation and changing imbibition capillary pressure;

determining a waterflood residual oil saturation ($S_{orw}$) of the core sample, the waterflood residual oil saturation associated with a point on the outlet-face saturation curve where the best-fit straight line deviates from the outlet-face saturation curve, wherein the waterflood residual oil saturation ($S_{orw}$) represents the ratio of the volume of the oil trapped in pores of the reservoir core sample under waterflooding to the total volume of the pores of the reservoir core sample; and providing the waterflood residual oil saturation ($S_{orw}$).

18. The computer-readable medium of claim 17, wherein testing the reservoir core sample to obtain a set of average water saturation ($S_{w,avg}$) and imbibition capillary pressure ($P_{ci}$) data points comprises:

determining average water saturation ($S_{w,avg}$) data points from measured volumes of expelled oil from the reservoir core sample for a set of rotational speeds of the centrifuge test; and determining imbibition capillary pressure ($P_{ci}$) using the following equation:

$$P_{ci} = \frac{1}{2}\Delta\rho\omega^2(r_3^2 - r_1^2);$$

where Δρ is a density difference between oil and water, ω is a rotational speed of the centrifuge of the centrifuge test, $r_3$ is a distance between an inlet end of the reservoir core sample and a rotational axis of the centrifuge, $r_1$ is the distance between an outlet end of the reservoir core sample and the rotational axis of the centrifuge.

19. The computer-readable medium of claim 17, wherein applying a best-fit smoothing function to the data points to obtain a best-fit average saturation curve comprises plotting the following equation for average water saturation ($S_{w,avg}$):

$$S_{w,avg} = 1 - a + \frac{1}{P_{ci}}\{b[1 - \exp(cP_{ci})] + d[1 - \exp(eP_{ci})]\};$$

where a, b, c, d, and e are best-fit matching parameters, and wherein parameters a and b affect a high-$P_{ci}$ section of the best-fit average saturation curve, parameters d and e affect a low-$P_{ci}$ section of the best-fit average saturation curve, and parameter c affects a transition section of the best-fit average saturation curve between the high-$P_{ci}$ section and the low-$P_{ci}$ section.

20. The computer-readable medium of claim 19, wherein applying a best-fit smoothing function to the data points to obtain the best-fit average saturation curve comprises applying a non-linear regression to the data points to obtain the best-fit average saturation curve.

21. The computer-readable medium of claim 19, wherein converting the best-fit average saturation curve to the outlet-face saturation curve comprises plotting the following equation for outlet water saturation ($S_{w,outlet}$):

$$S_{w,outlet} = S_{w,avg} + P_{ci} \times \frac{dS_{w,avg}}{dP_{ci}};$$

where $dS_{w,avg}/dP_{ci}$ is the derivative of the equation for average water saturation ($S_{w,avg}$), wherein plotting the equation for outlet water saturation ($S_{w,outlet}$) provides a true laboratory negative imbibition capillary pressure ($P_{ci}$) curve.

22. The computer-readable medium of claim 21, wherein determining the waterflood residual oil saturation ($S_{orw}$) of the core sample, where the waterflood residual oil saturation is associated with a point on the outlet-face saturation curve where the best-fit straight line deviates from the outlet-face saturation curve, comprises identifying the point on the outlet-face saturation curve corresponding to $dS_{w,avg}/dP_{ci}$ being equal to approximately 0.01.

* * * * *

UNITED STATES PATENT AND TRADEMARK OFFICE
CERTIFICATE OF CORRECTION

PATENT NO. : 11,940,437 B2
APPLICATION NO. : 16/638014
DATED : March 26, 2024
INVENTOR(S) : Yildiray Cinar, Tony R. Pham and Naseem J. Al-Dawood It is certified that error appears in the above-identified patent and that said Letters Patent is hereby corrected as shown below:

In the Claims

Column 18, Line 33, Claim 6, please replace "$dS_{w,avg}/d/P_{ci}$" with -- $dS_{w,avg}/dP_{ci}$ --.

Column 20, Line 33, Claim 17, please replace "(Pc')" with -- ($P_{ci}$) --.

Signed and Sealed this
Fourteenth Day of May, 2024

Katherine Kelly Vidal
*Director of the United States Patent and Trademark Office*